United States Patent [19]

Wollweber et al.

[11] 4,018,814
[45] Apr. 19, 1977

[54] AROMATIC AMIDES AND CARBOMATES OF PHENYLAMIDINES

[75] Inventors: Hartmund Wollweber, Wuppertal-Elberfeld, Germany; Winfried Flucke, Beenleigh Qu., Australia

[73] Assignee: Bayer Aktiengesellschaft, Germany

[22] Filed: Apr. 18, 1975

[21] Appl. No.: 569,565

Related U.S. Application Data

[62] Division of Ser. No. 398,692, Sept. 19, 1973, Pat. No. 3,911,010, which is a division of Ser. No. 151,581, June 9, 1971, Pat. No. 3,818,070.

[30] Foreign Application Priority Data

June 13, 1970 Germany .......................... 2029298

[52] U.S. Cl. ......................... 260/471 C; 260/453 R; 260/465 C; 260/465 D; 260/479 R; 260/558 P; 260/559 B; 260/501.14; 424/300; 424/304; 424/311; 424/324

[51] Int. Cl.² ................ C07C 101/62; A61K 31/27

[58] Field of Search ..... 260/558 P, 564 RF, 453 R, 260/465 C, 465 D, 479 R, 559 B, 471 C, 501.14

[56] References Cited

UNITED STATES PATENTS

| | | | |
|---|---|---|---|
| 3,164,633 | 1/1965 | Clemens | 260/558 P |
| 3,542,853 | 11/1970 | Peissker et al. | 260/564 RF X |
| 3,769,274 | 10/1973 | Wollweber et al. | 260/239 BF |
| 3,855,292 | 12/1974 | Wollweber et al. | 260/564 RF |
| 3,898,277 | 8/1975 | Duerr | 260/471 C X |
| 3,935,250 | 1/1976 | Pissiotas | 260/471 C X |
| 3,941,829 | 3/1976 | Pissiotas et al. | 260/471 C |

*Primary Examiner*—Robert V. Hines
*Assistant Examiner*—Thomas A. Waltz

[57] ABSTRACT

N-Phenylacetamidines bearing an acylamino group in the phenyl ring have anthelmintic activity and are effective against nematodes and cestodes. A representative embodiment is N-(4-carbophenoxyaminophenyl)-N′,N′-dimethylacetamidine.

10 Claims, No Drawings

AROMATIC AMIDES AND CARBOMATES OF PHENYLAMIDINES

This is a division of application Ser. No. 398,692 filed Sept. 19, 1973, which in turn is a division of Ser. No. 151,581 filed June 9, 1971, now U.S. Pat. No. 3,818,070.

The present invention relates to new aminophenylamidines, to processes for their production, and to their pharmaceutical use. These new compounds are useful as paraciticides, especially as anthelmintics.

Some acylaminophenylformamidines, such as N-(p-acetamidophenyl)-N',N'-dimethylformamidine (U.S. Pat. No. 3,184,482) and N-phenyl-acetamidines, such as N-(p-chlorophenyl)-N',N'-dimethylacetamidine, are already known. These compounds are however inactive against the helminths mentioned below.

This invention provides aminophenylamidines of the general formula:

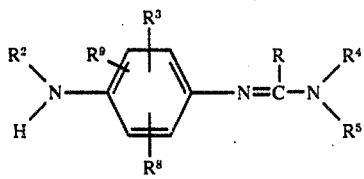

(1)

in which
R is a straight, cyclic, of 3 to 7 carbon atoms or branched-chain alkyl, alkenyl or alkoxy group;
$R^2$ is a —$COR^6$ group or an —$SO_2R^7$ group in which $R^6$ is a hydrogen atom; a straight-or branched-chain alkyl, alkenyl, alkynyl, alkoxy, alkenyloxy, alkynyloxy, alkoxyalkyloxy or alkoxyalkyl group; a cycloakyl group or a cycloalkenyl group containing one or two double bonds, which cycloalkyl and cycloalkenyl groups can be substituted by one or more alkyl groups; a cycloalkylalkyl, benzocycloalkylalkyl, tetrahydrofuryl, tetrahydrofurfuryl or tetrahydropyranyl group which can be substituted by one or more alkyl groups; a trifluoromethyl group; an alkyl group substituted by one or more halogen atoms or by one or more cyano, hydroxy, acyloxy, alkoxy or oxo-groups; a carbalkoxy- alkyl group; a cycloalkyl-alkoxy group; a cycloalkoxy- or tetrahydrofurylalkoxy group; a phenylalkoxy, phenoxyalkoxy, phenoxy, phenylalkyl, phenyl, phenylalkenyl or naphthyl group, in which the aromatic ring can be substituted by one or more alkyl, alkenyl, alkoxy, hydroxy, acyloxy, nitro, trifluoromethyl, cyano, carbethoxy, alkylsulphonyl, acylamino or alkylsulphonyl-amino groups or fluorine, chlorine or bromine atoms; a heteroaromatic ring system which can be substituted by one or more alkyl groups; a furylalkyl, thienylalkyl, indolylalkyl, furylalkoxy or thienylalkoxy, group which can be substituted by one or more alkyl groups; or a phenylalkyl group, the alkyl part of which is substituted by a hydroxy, acyloxy, or alkoxy group; and
$R^7$ is a straight- or branched-chain alkyl or alkenyl group, an aralkyl group, a cycloalkyl group, or a cycloalkyl-alkyl group;
$R^3$, $R^8$ and $R^9$ be the same or different and is each a hydrogen or halogen atom or a straight- or branched-chain alkyl, alkenyl or alkoxy group or a cyano or trifluoromethyl group;
$R^4$ is a straight- or branched-chain alkyl, alkenyl, alkynyl or alkoxy group; and
$R^5$ is a straight- or branched-chain alkyl or alkenyl group or a cyclo-alkyl group; and their salts.

These compounds are useful for combating parasites, especially helminths.

The alkyl groups R as well as the alkyl part of the alkoxy groups R, preferably contain 1 to 5, especially 1 or 2, carbon atoms, and the alkenyl group R preferably contains 2 to 5 carbon atoms.

The cycloalkyl group $R^5$ preferably contains 3 to 7, more preferably 5 to 7, carbon atoms.

The alkyl groups, and the alkyl component of the alkoxy groups $R^3$, $R^8$ and $R^9$ preferably contain 1 to 4, especially 1 or 2, carbon atoms. The alkenyl groups $R^3$, $R^8$ and $R^9$ preferably contain 2 to 4 carbon atoms.

Halogens $R^3$, $R^8$ and $R^9$ are generally fluorine, chlorine and bromine, but preferably chlorine.

Alkyl radicals, as well as the alkyl constituents of the alkoxy groups $R^4$, preferably contain 1 to 4, especially 1 or 2, carbon atoms. Alkenyl and alkynyl radicals $R^4$ preferably contain 2 to 4 carbon atoms.

Alkyl $R^5$ preferably contain 1 to 5, especially 1 or 2, carbon atoms, and alkenyl groups $R^5$ preferably contain 2 to 5 carbon atoms.

The alkyl groups, and the alkyl component of the alkoxy groups $R^6$, preferably contain 1 to 6, especially 1 to 3, carbon atoms. The alkenyl and alkynyl groups $R^6$, and the alkenyl and alkynyl components of the alkenyloxy and alkynyloxy groups $R^6$, preferably contain 2 to 6, especially 2 or 3, carbon atoms. Alkoxyalkyloxy and alkoxyalkyl groups $R^6$ preferably each contain 2 to 6, preferably 2 or 3, carbon atoms. Cycloalkyl groups $R^6$ contain 3 to 7, preferably 3 to 6, carbon atoms. The cycloalkyl groups $R^6$ can contain one or more, preferably one, alkyl group having preferably 1 to 4, especially 1 or 2, atoms.

The cycloalkylalkyl groups $R^6$ generally contain 3 to 7, preferably 5 to 6, carbon atoms in the cycloalkyl part, and preferably 1 to 4, especially 1 or 2, carbon atoms in the alkyl part. The benzoylcycloalkylalkyl groups $R^6$ preferably contain 1 to 4, especially 1 or 2, carbon atoms in each alkyl part.

The cycloalkylalkyl, benzocycloalkylalkyl and tetrahydrofuryl, tetrahydrofurfuryl and tetrahydropyranyl groups $R^6$ can be substituted by one or more alkyl groups with, preferably, 1 to 4, especially 1 or 2, carbon atoms. The alkyl groups $R^6$ substituted by one or more, preferably 1, halogen atom, especially fluorine, chlorine or bromine, or by one or more, especially one, nitrile, hydroxyl or oxo group, preferably contain 1 to 4, especially 1 or 2, carbon atoms. The carbalkoxyalkyl groups $R^6$ generally contain 1 to 4, preferably 1 or 2, carbon atoms in the alkyl part. The cycloalkylalkoxy groups $R^6$ generally contain 3 to 7, preferably 5 or 6, carbon atoms in the cycloalkyl part and 1 to 4, preferably 1 or 2, carbon atoms in the alkyl or alkoxy component. The cycloalkoxy groups $R^6$ generally contain 3 to 7, preferably 5 or 6, carbon atoms. The alkyl or alkoxy components of the tetrahydrofurylalkoxy group, phenylalkoxy group, phenoxyalkoxy group and phenylalkyl group mentioned under $R^6$ preferably contain 1 to 4, especially 1 or 2, carbon atoms. The phenylalkenyl groups $R^6$ preferably contain 2 to 4 carbon atoms in the alkenyl part.

If R⁶ represents an aromatic radical (phenyl or naphthyl), or if the radicals R⁶ contain aromatic constituents (phenyl or naphthyl), the aromatic structures can contain one or more, preferably 1 or 2, substituents. Possible substituents are alkyl radicals with 1 to 4, preferably 1 or 2, carbon atoms, alkenyl radicals with 2 to 4 carbon atoms, alkoxy radicals with 1 to 4, preferably 1 or 2, carbon atoms, acyloxy radicals with 2 to 4, preferably 2 or 3, carbon atoms, alkylsulphonyl radicals with 1 to 4, preferably 1 or 2, carbon atoms, acylamino radicals with 2 to 4, preferably 2, carbon atoms, and alkylsulphonylamino radicals with 1 to 4, preferably 1 or 2, carbon atoms.

The hetero-aromatic O-, S- or N-containing ring system R⁶ generally comprises a 5- or 6-membered hetero-aromatic ring, which can contain 1 to 3, preferably 1 or 2, hetero-atoms, such as oxygen, sulphur and nitrogen; a benzene ring can be fused to the hetero-aromatic ring. The hetero-aromatic ring system can be substituted by one or more, preferably 1 or 2, alkyl groups with 1 to 4, preferably 1 or 2, carbon atoms. The furyl, thienyl, isoxazolyl, pyrimidinyl, imidazolyl, pyrazolyl, indolyl, thianaphthyl, quinolyl, phenothiazinyl, thiadiazolyl and thiazolyl groups may be mentioned as examples.

Furylalkyl, thienylalkyl, indolylalkyl, furylalkyloxy and thienylalkyloxy groups R⁶ generally possess 1 to 4, preferably 1 or 2, carbon atoms in the alkyl or alkoxy component. The hetero-aromatic constituents can be substituted by one or more, preferably 1 or 2, alkyl groups with 1 to 4, preferably 1 or 2, carbon atoms.

Alkyl groups $R^7$ preferably contain 1 to 6, especially 1 or 2, carbon atoms, and alkenyl groups $R^7$ preferably contain 2 to 6 carbon atoms.

Aralkyl groups $R^7$ generally contain 6 or 10 carbon atoms in the aryl part and 1 to 4, preferably 1 or 2, carbon atoms in the alkyl part.

The cycloalkyl groups, as well as the cycloalkyl constituent of the cycloalkyl-alkyl group $R^7$, generally contain 3 to 7, preferably 5 or 6, ring members. The cycloalkyl-alkyl group $R^7$ generally possesses 1 to 4, preferably 1 or 2, carbon atoms in the alkyl part.

The aminophenylamidines according to the invention are basic in character. They can be used as free bases or in the form of their salts, for example hydrohalides, preferably hydrochlorides, sulphates, phosphates, nitrates, acetates or naphthalenedisulphonates.

Particularly preferred compounds are those of the general formula:

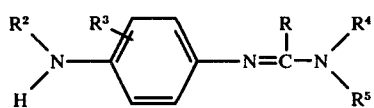

in which
R is a methyl or ethyl group;
$R^2$ is a —COR⁶ group or an —SO₂R⁷ group, in which R⁶ is a hydrogen atom, a straight- or branched-chain alkyl or alkenyl group containing up to 3 carbon atoms and optionally substituted by a trifluoromethyl or methoxy group; a cycloalkyl group with 3 to 5 carbon atoms; a furyl group; a 5-methylisoxazolyl group; a phenyl group; or an alkoxy or alkynyloxy group containing up to 4 carbon atoms and optionally substituted by a methoxy group; and R⁷ is a methyl or ethyl group;

R³ is a hydrogen or chlorine atom;
R⁵ is a hydrogen atom or a methyl or ethyl group;
R⁴ is a methyl, ethyl or methoxy group; and their physiologically tolerated salts.

Preferred salts of the new compounds are the hydrochlorides.

The invention also provides a number of processes designated as (a), (b), (c), (d), (e) and (f) for the production of the new aminophenylamidines and salts.

In process (a), an aniline derivative of the general formula:

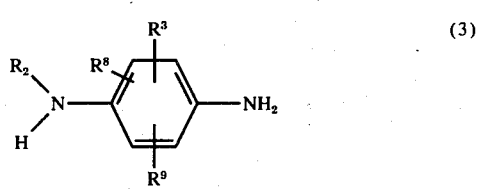

is reacted with a carboxylic acid amide or thioamide of the general formula:

in which general formula W is oxygen or sulphur and R to R⁵, R⁸ and R⁹ are as defined above, or with a salt or reactive derivative thereof. The reaction may be carried out in the presence of a condensation agent and optionally of an inert solvent. The reaction products may be isolated in the form of a salt or in the form of the free base and then converted if necessary into any other desired salt in any suitable manner.

As reactive derivatives there may be used, for example, compounds obtained by reaction of an amide or thioamide of the general formula (4) with an organic acid (for example, hydrochloric acid, boron trichloride or sulphuric acid), with an inorganic or organic acid halide (for example, phosphorus oxychloride, phosphorus pentachloride, phosgene, thionyl chloride, benzoyl bromide, p-toluenesulphonyl chloride or a mixture of phosgene/aluminum chloride or phosgene/hydrogen chloride or phosgene, or phosphorus oxychloride), with a trialkyloxonium fluoborate having 1 to 5 carbon atoms per alkyl group, with a dialkyl sulphate having 1 to 5 carbon atoms per alkyl group, or with an alkyl halide having 1 to 5 carbon atoms.

Further reactive amide derivatives that may be used are acetals and thioacetals of the general formula:

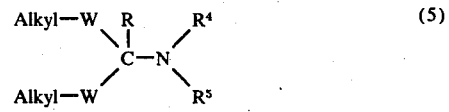

in which W, R, R⁴ and R⁵ are as defined above and "Alkyl" denotes an alkyl group having up to 4 carbon atoms.

As examples of condensation agents which can be employed in process (a), there may be mentioned: inorganic acids (for example, hydrochloric acid, boron trichloride or sulphuric acid); inorganic or organic acid halides (for example, phosphorus oxychloride, phosphorus pentachloride, phosgene, thionyl chloride, benzoyl bromide, p-toluenesulphonyl chloride or a mixture of phosgene/aluminum chloride or phosgene/hydrogen chloride or phosgene, phosphorus oxychloride); trialkyloxonium fluoborates, (1 to 5 carbon atoms per alkyl group); dialkyl sulphates (1 to 5 carbon atoms per alkyl group); and alkyl halides (1 to 5 carbon atoms).

In the case of the reaction of thioamides (general formula (4); W=sulphur), a desulphurising agent, for example, HgO, Ag₂O or Hg(CN)₂, can advantageously be used additionally to these condensation agents, or without these condensation agents.

The reactants are preferably employed in the stoichiometrically required amounts.

As solvents, it is possible to use any inert organic solvents; these include aromatic, optionally halogenated, hydrocarbons, for example, benzene, toluene and dichlorobenzene; optionally chlorinated aliphatic hydrocarbons for example, methylene chloride and chloroform; tetramethylenesulphone, and lower aliphatic alcohols; for example, methanol and ethanol.

The reactants are preferably brought together at room temperature (about 20° C) and can be warmed to between 30° and 150° C, preferably 70° to 120°, in order to complete the reaction.

The success of the reaction does not depend on the sequence in which the reactants are brought together. The new compounds are isolated in the usual manner.

Process (b) comprises reacting an amine of the general formula:

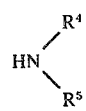

(6)

with an anilide of the general formula:

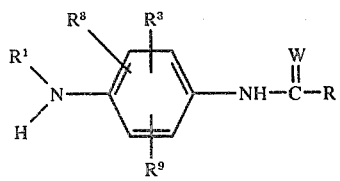

(7)

in which general formulae W, R to R⁵, R⁸ and R⁹ are as defined above, or with a salt or a reactive derivative thereof.

The reaction is optionally carried out in the presence of a solvent and optionally in the presence of a condensation agent.

Reactive anilide derivatives suitable for use in process (b) are, for example, those obtained by the reaction of an anilide of general formula (7) with an inorganic acid (such as hydrogen chloride, boron trichloride or sulphuric acid), with an inorganic or organic acid halide (such as phosphorus oxychloride, phosphorus pentachloride, phosgene, thionyl chloride, benzoyl bromide, p-toluenesulphonyl chloride or a mixture of phosgene/aluminum chloride, or phosgene/hydrogen chloride or phosgene, phosphorus oxychloride), with a trialkyloxonium fluoborates having up to 1 to 5 carbon atoms in each alkyl group, with a dialkyl sulphate having up to 5 atoms in each alkyl group or with an alkyl halide having up to 5 carbon atoms.

Other reactive anilide derivatives suitable for use in process (b) are acetals and thioacetals of the general formula:

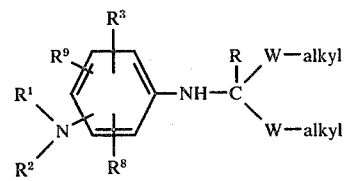

(8)

in which R, R¹, R², R³, R⁸, R⁹ and W are as defined above, Alkyl denotes an alkyl group having up to 4 carbon atoms, and the two alkyl groups together can form a 5- or 6- or 7-membered ring.

Further reactive anilide derivatives suitable for use in process (b) are iminoethers of the general formula:

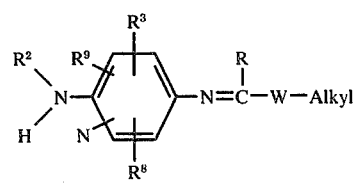

(9)

in which R, R¹, R², R³, R⁸, R⁹ and W are as defined above and Alkyl denotes an alkyl group having up to 4 carbon atoms.

Process (b) is carried out under the same reaction conditions (molar ratio, temperature, condensation agent and solvent) as process (a).

Process (c) comprises heating an arylisocyanate of the general formula:

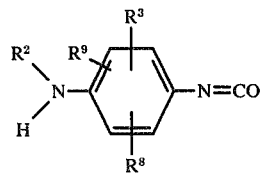

(10)

with an amide or thioamide of the general formula:

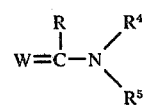

(11)

in which general formulae W, R to R⁵, R⁸ and R⁹ are as defined above.

The progress of the reaction can be followed from the accompanying evolution of CO₂ or COS.

Process (d) comprises heating a compound of the general formula:

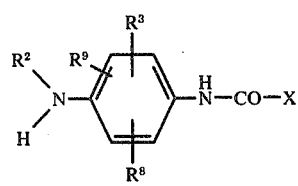

(12)

with an amide or thioamide of the general formula:

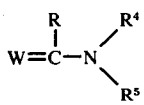
(11)

in which general formulae R to $R^5$, $R^8$, $R^9$ and W are as defined above.

In the processes (c) and (d), the reactants are preferably reacted in molar ratios.

The reactions are expediently carried out at temperatures between 80° and 200° C, preferably between 110° and 180° C, optionally in the presence of an inert organic solvent.

As examples of such solvents suitable for use in process (c) or (d) there may be mentioned benzene, toluene and dichlorobenzene.

Process (e) is applicable to those aminophenylamidines of the invention in which $R^4$ and $R^5$ are alkyl or alkenyl groups, and comprises reacting a phenylamidine of the general formula:

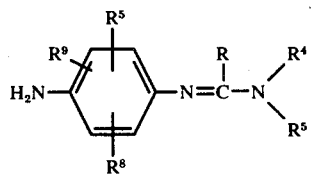
(13)

with an alkylating agent of the general formula:

$$B - R^{10} \qquad (14)$$

in which general formulae R, $R^2$, $R^3$, $R^8$ and $R^9$ are as defined above, $R^{10}$ is a straight- or branched-chain alkyl or alkenyl group, and B is a reactive ester group or a halogen atom.

Preferred halogen atoms B are chlorine, bromine and iodine. Preferred reactive ester groups are arylsulphonyloxy and alkylsulphonyloxy groups, for example, methanesulphonyloxy and toluenesulphonyloxy groups.

The compounds of the general formula (13) can, for example, be obtained in a known manner by the reaction of an aniline derivative of general formula (3) with a nitrile of the general formula:

$$R - CN \qquad (15)$$

in which R is as defined above, optionally in the presence of a condensation agent for example, aluminum chloride.

The reactants in process (e) are preferably employed in molar amounts. The reaction takes place at temperatures between 0° and 120° C, and is preferably carried out at 20° to 80° C, in the presence of an inert organic solvent.

Ethers, for example, diethyl ether or tetrahydrofurane and alkylnitriles for example, acetonitrile are, for example, suitable as solvents. It can, at times, also be desirable to add an acid-binding agent, for example, an alkali metal carbonate or an alkaline earth metal carbonate, preferably sodium or potassium carbonate.

Finally, process (f) comprises reacting an aminophenylamidine of the general formula:

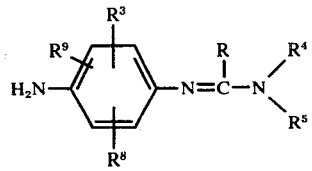
(16)

with an acylating or sulphonylating agent of the general formula:

$$Y - Z \qquad (17)$$

in which general formulae R, $R^4$, $R^5$, $R^8$ and $R^9$ are as defined above, Z is a group $-COR^6$ or $-SO_2R^7$, in which $R^6$ and $R^7$ are as defined above, and Y is a reactive acid group or a halogen atom optionally in the presence of a solvent and optionally in the presence of an acid-binding agent.

Halogen atoms Y are preferably chlorine and bromine atoms. When Z is a $-COR^6$ group, Y is a $-O-CO-R^6$ or $-OR^6$ group in which $R^6$ and $R^6$ are as defined above for $R^6$ and can be the same or different to $R^6$ in the acylating or sulphonylating agent of general formula (17).

If Z is an $-SO_2R^7$ group, Y is a halogen atom.

As the alkylating or sulphonylating agent Y–Z, there may especially be mentioned: lower alkylpyrocarbonic acid esters with 1 to 4 carbon atoms in the alkyl part; lower chloroformic acid alkyl esters with, preferably, 1 to 4 carbon atoms in the alkyl component; lower alkylcarboxylic acid chlorides and bromides with, preferably, 1 to 4 carbon atoms in the alkyl group; formic acid alkyl esters with 1 to 4 carbon atoms in the ester part; methanesulphonic acid chloride; benzoyl chloride and acetic anhydride; or mixed anhydrides, such as formic-acetic anhydride.

In process (f), the reactants are preferably brought together in molar amounts.

The reaction temperatures are expediently 0° to 120° C, preferably 20° to 90° C.

As solvents, it is possible to employ any solvent that is inert during this reaction. Lower aliphatic alcohols for example, methanol or ethanol aromatic hydrocarbons for example, benzene and toluene, petroleum ether, chlorinated hydrocarbons for example, chloroform and methylene chloride, as well as tetramethylenesulphone, may be mentioned as examples.

The aminophenylamidines (16) can for example be obtained from the nitrophenylamidines and/or their salts, of the general formula:

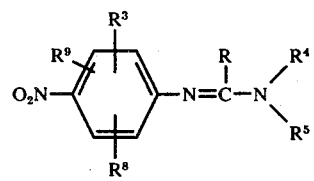
(18)

in which R, $R^3$, $R^4$, $R^5$, $R^8$ and $R^9$ are as defined above by reduction, in any suitable manner.

The starting compounds required for the production of the new compounds are known or are obtainable by processes known in the art.

The following may be mentioned as examples of the starting material: 2-, 3- or 4-carbethoxyamino-aniline;

carbomethoxyamino-aniline; carbisopropoxyamino-aniline; carbutoxyamino-aniline; methylsulphonylamino-aniline; ethylsulphonylamino-aniline; acetamino-aniline; propionylaminoaniline; butyrylamino-aniline; isovaleroyamino-aniline; formylamino-aniline; dimethylsulphamoyl-aniline; acryloylamino-aniline; methacryloylamino-aniline; crotonylaminoaniline; methoxypropionyl-aniline; ethoxyacetylamino-aniline; methoxyacetylamino-aniline; carballyloxyamino-2-chloroaniline; 4-carbethoxyamino-3-chloro-5-methyl-aniline; 4-carbethoxy-amino-3,5-dimethylaniline; 4-(N-carbethoxy-N-methyl-amino)-aniline; 4-carbethoxyamino-3-bromoaniline; 4-carbethoxyamino-trifluoromethylaniline; 2,5-dichloro-4-acetamino-aniline; 2,5-dichloro-4-carbethoxyamino-aniline; 3,5-dichloro-4-carbethoxyaniline; 2-chloro-4-carbethoxy-5-methylaniline; 5-chloro-4-carbethoxy-2-methyl-aniline and 2,4-dimethyl-5-carbethoxyamino-aniline; N-(4-nitrophenyl)-N', N'-dimethyl-acetamidine; N-(4-nitrophenyl)-N',N'-diethylacetamidine; N-(4-nitrophenyl)-N',N'-dimethylpropionamidine; N-(4-nitrophenyl)-N',N'-diethylpropionamidine and N-(4-nitrophenyl)-N'-ethyl-N'-methyl-acetamidine.

The salts of the aminophenylamidines according to the invention can be obtained from the free bases in the usual manner.

The production of the new compounds by processes according to the invention is illustrated in the Examples which follow.

All temperatures are given in °C.

EXAMPLE 1

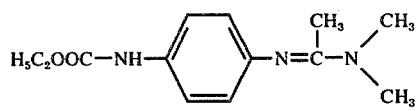
(19)

4-Carbethoxyamino-aniline and 46.6 g of N,N-dimethylacetamide are dissolved in 1000 ml of toluene. 79.5 g of phosphorus oxychloride are added dropwise thereto at 20°, and the mixture is stirred for 90 minutes at 20° and heated for 4 hours under reflux. After decanting off the toluene, the residue is taken up in a mixture of water and chloroform, sodium hydroxide solution is added whilst cooling, inorganic products are filtered off, and the organic phase is separated off. After evaporating the organic phase, 101 g of crude N-(4-carbethoxyaminophenyl)-N',N'-dimethyl-acetamidine are obtained; this is recrystallised from ethyl acetate. Melting point 130° – 131°, yield 84 g. The hydrochloride is obtained by dissolving the compound in ether and adding a solution of hydrochloric acid in ether, and is recrystallised from a mixture of ethyl acetate and alcohol. Melting point 222° (decomposition). The same compound is also obtained if phosgene or p-toluenesulphonyl chloride are used as condensation agents.

The following compounds are prepared by proceeding analogously: N-(4-carbomethoxyaminophenyl)-N',N'-dimethylacetamidine, melting point 137° – 139°;

N-(4-carbethoxyaminophenyl)-N',N'-dimethylpropionamidine, melting point 114° – 115°;

N-(4-carbethoxyaminophenyl)-N',N'-dimethyl-butyramidine;

N-(4-carbethoxyaminophenyl)-N',N'-diethyl-isobutyramidine;

N-(4-carbethoxyaminophenyl)-N',N'-dimethyl-pivalylamidine;

N-(4-carbethoxyaminophenyl)-N',N'-dimethyl-valeramidine;

N-(4-carbethoxyaminophenyl)-N',N'-dimethyl-acrylamidine;

N-(4-carbethoxyaminophenyl)-N',N'-dimethyl-crotylamidine;

N-(4-carbethoxyaminophenyl)-N',N'-dimethyl-$\beta,\beta$-dimethylacrylamidine;

N-(4-carbethoxyaminophenyl)-N',N'dimethyl-$\alpha$-methacrylamidine;

N-(4-carbethoxyaminophenyl)-N',N'-dimethy-$\alpha$-methoxyacetamidine;

N-(4-carbethoxyaminophenyl)-N',N'-dimethyl-ethoxyacetamidine;

N-(4-carbethoxyaminophenyl)-N',N'-dimethyl-cyclopropylcarboxamidine;

N-(4-carbethoxyaminophenyl)-N',N'-dimethylcyclobutylcarboxamidine;

N(4-carbethoxyaminophenyl)-N',N'-dimethyl-cyclopentylcarboxamidine;

N-(4-carbethoxyaminophenyl)-N',N'-dimethyl-cyclohexylcarboxamidine;

N-(4-carbethoxyaminophenyl)-N',N'-diethylacetamidine; melting point 88° – 90°;

N-(4-carbethoxyaminophenyl)-N'-ethyl-N-methyl-acetamidine, melting point 105° – 107°; hydrochloride, melting point 195° – 196°;

N-(4-carbethoxyaminophenyl)-N'-methyl-N'-propyl-acetamidine;

N-(4-carbethoxyaminophenyl)-N'-ethyl-N'-propyl-acetamidine;

N-(4-carbethoxyaminophenyl)-N'-methyl-N'-isopropyl-acetamidine;

N-(4-carbethoxyaminophenyl)-N'-allyl-N'-methyl-acetamidine;

N-(4-carbethoxyaminophenyl)-N'-crotyl-N'-methyl-acetamidine;

N-(4-carbethoxyaminophenyl)-N'-methallyl-N'-methyl-acetamidine;

N-(4-carbethoxyaminophenyl)-N'-methyl-N'-($\beta$-methyl-vinyl)-acetamidine;

N-(4-carbethoxyaminophenyl)-N'-methyl-N'($\beta,\beta$-dimethyl-vinyl)-acetamidine;

N-(4-carbethoxyaminophenyl)-N',N'-diallyl-acetamidine;

N-(4-carbethoxyaminophenyl)-N',N'-dicrotyl-acetamidine;

N-(4-carbethoxyaminophenyl)-N'-methyl-N'-propynyl-acetamidine;

N-(4-carbethoxyaminophenyl)-N'-methyl-N'-cyclopentylacetamidine;

N-(4-carbethoxyaminophenyl)-N'-methyl-N'-cyclohexyl-acetamidine; and

N-(4-carbethoxyaminophenyl)-N'-methyl-N'-cycloheptylacetamidine.

EXAMPLE 2

15.3 g of pyrocarbonic acid ethyl ester are added dropwise to 17.7 g of N-(4-aminophenyl)-N',N'-dimethylacetamidine (melting point 92° – 93°) dissolved in 200 ml of tetrahydrofurane, the mixture is heated to 50° for one hour and evaporated in vacuo, and the N-(4-carbethoxyaminophenyl)-N',N'-dimethyl-acetamidine, described in Example 1, is recrystallised from ethyl acetate. Melting point 130° – 131°.

The N-(4-aminophenyl)-N',N'-dimethylacetamidine used as the starting material is obtained by catalytic hydrogenation of N-(4-nitrophenyl)-N',N'-dimethylacetamidine (melting point 94° – 95°), or of its hydrochloride, with Raney nickel as the catalyst.

EXAMPLE 3

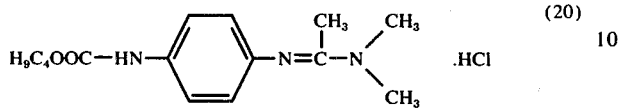

(20)

13.7 g of chloroformic acid n-butyl ester are added dropwise, at 20°, to 17.7 g of N-(4-aminophenyl)-N,N-dimethyl-acetamidine, dissolved in 150 ml of ethanol, and the mixture is heated for one hour under reflux and evaporated in vacuo. After recrystallisation from ethanol/ethyl acetate, 25.5 g of pure N-(4-carbobutoxy-aminophenyl)-N',N'-dimethylacetamidine hydrochloride, melting point 210° – 212° (decomposition), are obtained.

The following are obtained by analogous processes:
N-(4-carboisopropoxyaminophenyl)-N,N'-dimethyl-acetamidine hydrochloride, melting point 232° – 235°;
N-(4-carbopropoxyaminophenyl)-N',N'-dimethyl-acetamidine hydrochloride, melting point 205° – 206°;
N-(4-carboisobutoxyaminophenyl)-N',N'-dimethyl-acetamidine hydrochloride;
N-(4-carballyoxyaminophenyl-N',N'-dimethyl-acetamidine hydrochloride;
N-(4-carbocrotyloxyaminophenyl)-N',N'-dimethyl-acetamidine hydrochloride;
N-(4-carbomethallyloxyaminophenyl)-N',N'-dimethyl-acetamidine hydrochloride;
N-(4-carbopropynyloxyaminophenyl)-N',N'-dimethyl-acetamidine hydrochloride; melting point,(crude) 205°– 207°; the free base, melting point 126° – 128° is obtained therefrom by adding sodium hydroxide solution;
N-[4-carbo-(3,3-dimethylhexyloxy)aminophenyl]-N',N'-dimethylacetamidine, melting point 128°;
N[4-carbo-(β-methoxyethyloxy)-aminophenyl]-N',-N'-dimethylacetamidine hydrochloride, melting point 189° – 191° (decomposition); free base; melting point 126° – 128°;
N-(4-carbocyclopropyloxyaminophenyl)-N',N'-dimethyl-acetamidine hydrochloride;
N(4-carbocyclobutyloxyaminophenyl)-N',N'-dimethyl-acetamidine hydrochloride;
N-(4-carbocyclopentyloxyaminophenyl)-N',N'-dimethyl-acetamidine hydrochloride;
N-(4-carbocyclohexyloxyaminophenyl)-N',N'-dimethyl-acetamidine hydrochloride;
N-(4-carbocyclohexylmethyloxyaminophenyl)-N',-N'-dimethyl-acetamidine hydrochloride;
N-(4-carbobenzoxyaminophenyl)-N',N'-dimethyl-acetamidine hydrochloride;
N-(4-carbophenethyloxyaminophenyl)-N',N'-dimethyl-acetamidine hydrochloride;
N-(4-carbotetrahydrofuryloxyaminophenyl)-N',N'-dimethyl-acetamidine hydrochloride;
N-(4-carbotetrahydrofurfuryloxyaminophenyl)-N',-N'-dimethyl-acetamidine hydrochloride;
N-(4-carbofurfuryloxyaminophenyl)-N',N'-dimethyl-acetamidine hydrochloride;
N-(4-carbothienyl(2)-methoxy-aminophenyl)-N',N'-dimethyl-acetamidine hydrochloride;
N-(4-carbophenoxy-aminophenyl)-N',N'-dimethyl-acetamidine hydrochloride, melting point 233° – 235°; and
N[4-carbo-(4-chlorophenoxy)-aminophenyl]-N',N'-dimethyl-acetamidine hydrochloride, melting point 236° – 238°.

EXAMPLE 4

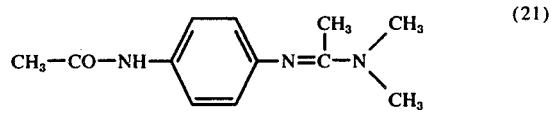

(21)

Following the method described in Example 1, reaction of 4-aminoacetanilide and dimethylacetamide in the presence of phosphorus oxychloride as the condensation agent yields N-(4-acetyl-aminophenyl-N',N'-dimethylacetamidine, melting point 132° – 134°, in a yield of 93% of theory; hydrochloride, melting point 258° – 260°.

The following are obtained by analogous processes:
N-(4-acetaminophenyl)-N',N'-dimethyl-propionamidine;
N-(4-acetaminophenyl)-N',N'-dimethyl-butyramidine;
N-(4-acetaminophenyl)-N',N'-dimethyl-isobutyramidine;
N-(4-acetaminophenyl)-N',N'-dimethyl-valeramidine;
N-(4-acetaminophenyl)-N',N'-dimethyl-pivalylamidine;
N-(4-acetaminophenyl)-N',N'-dimethyl-acrylamidine;
N-(4-acetaminophenyl)-N',N'-dimethyl-crotylamidine;
N-(4-acetaminophenyl)-N',N'-dimethyl-methallylamidine;
N-(4-acetaminophenyl)-N',N'-dimethyl-β,β-dimethylacrylamidine;
N-(4-acetaminophenyl)-N',N'-dimethyl-methoxyacetamidine;
N-(4-acetaminophenyl)-N',N'-dimethyl-ethoxyacetamidine;
N-(4-acetaminophenyl)-N',N'-dimethyl-cyclopropylcarboxamidine;
N-(4-acetaminophenyl)-N',N'-dimethyl-cyclobutyl-carboxamidine;
N-(4-acetaminophenyl)-N',N'-dimethyl-cyclopentyl-carboxamidine;
N-(4-acetaminophenyl)-N',N'-dimethyl-cyclohexyl-carboxamidine;
N-(4-acetaminophenyl)-N',N'-diethyl-acetamidine;
N-(4-acetaminophenyl)-N'-ethyl-N'-methyl-acetamidine;
N-(4-propionylaminophenyl)-N'-ethyl-N'-methyl-acetamidine;
N-(4-acetaminophenyl)-N'-methyl-N'-propyl-acetamidine;
N-(4-acetaminophenyl)-N-ethyl-N'-propyl-acetamidine;
N-(4-acetaminophenyl)-N'-methyl-N'-isopropyl-acetamidine;
N-(4-acetaminophenyl)-N'-allyl-N'-methyl-acetamidine;

N-(4-acetaminophenyl)-N'-methyl-N'-(β,β-dimethyl-vinyl)-acetamidine;
N-(4-acetaminophenyl)-N'-methyl-N'-cyclopentyl-acetamidine;
N-(4-acetaminophenyl)-N'-methyl-N'-cyclohexyl-acetamidine;
N-(4-acetaminophenyl)-N'-methyl-N'-cyclohexyl-acetamidine;
N-(4-acetaminophenyl)-N'-methyl-N'-cycloheptyl-acetamidine;
N-(4-cyclopentylcarbonylaminophenyl)-N',N'-dimethyl-acetamidine, hydrochloride, melting point 244° – 247°;
N-(4-cyclohexylmethylcarbonylaminophenyl)-N',N'-dimethyl-acetamidine;
N-(4-phenylacetylaminophenyl)-N',N'-dimethyl-acetamidine;
N-(4-phenethylcarbonylaminophenyl)-N',N'-dimethyl-acetamidine;
N-[4-tetrahydrofurfurylcarbonyl-(2)-aminophenyl]-N',N'-dimethyl-acetamidine;
N-[4-(5-methyltetrahydrofuryl-carbonyl-[2]-aminophenyl]-N',N'-dimethyl-acetamidine;
N-[4-(2-methyl-tetrahydrofuryl-carbonyl-[2]-aminophenyl]-N',N'-dimethyl-acetamidine;
N-[4-tetrahydrofurfuryl-carbonyl-(2)-aminophenyl]-N',N'-dimethyl-acetamidine;
N-[4-tetrahydropyranyl-carbonyl-aminophenyl]-N',N'-dimethyl-acetamidine;
N-(4-trifluoro-acetylaminophenyl)-N',N'-dimethyl-acetamidine, hydrochloride, melting point 273° – 274°;
N-(4-trichloro-acetylaminophenyl)-N',N'-dimethyl-acetamidine;
N-[4-(β,β,β-trichloropropionyl)-aminophenyl]-N',N'-dimethyl-acetamidine;
N-(4-carbethoxy-carbonylaminophenyl)-N',N'-dimethyl-acetamidine;
N-(4-carbethoxymethylene-carbonylaminophenyl)-N',N'-dimethyl-acetamidine;
N-(4-β-carbethoxyethylene)-carbonylaminophenyl)-N',N'-dimethyl-acetamidine;
N-(4-cyanomethylenecarbonylaminophenyl)-N',N'-dimethyl-acetamidine.

EXAMPLE 5

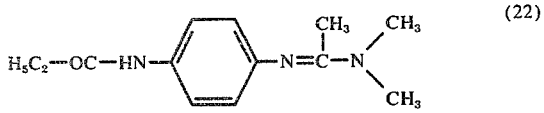

(22)

18.5 g of propionyl chloride are added dropwise to a solution of 35.4 g of N-(4-aminophenyl)-N',N'-dimethyl-acetamidine in 300 ml of toluene. The mixture was stirred for a further hour, and after evaporation and recrystallisation from ethanol/ethyl acetate, 43.5 g of N-(4-propionylaminophenyl)-N',N'-dimethyl-acetamidine hydrochloride, melting point 257° – 258°, are obtained. The free base is obtained therefrom by adding sodium hydroxide solution.

The following are obtained by analogous processes:
N-(4-butyrylaminophenyl)-N',N'-dimethyl-acetamidine;
N-(4-isobutyrylaminophenyl)-N',N'-dimethyl-acetamidine, hydrochloride, melting point 248° – 250°;
N-(4-pivaloylaminophenyl)-N',N'-dimethyl-acetamidine;
N-(4-valeroylaminophenyl)-N',N'-dimethyl-acetamidine;
N-(acryloylaminophenyl)-N',N'-dimethyl-acetamidine;
N-(crotonoylaminophenyl)-N',N'-dimethyl-acetamidine;
N-(methacryloylaminophenyl)-N',N'-dimethyl-acetamidine, hydrochloride, melting point 216°–218°;
N-propynylcarbonylaminophenyl)-N',N'-dimethyl-acetamidine;
N-(methoxyacetylaminophenyl)-N',N'-dimethyl-acetamidine, hydrochloride, melting point 205°– 207° (decomposition);
N-(cyclopropylcarbonylaminophenyl)-N',N'-dimethyl-acetamidine, hydrochloride, melting point 282° – 284°;
N-(cyclobutylcarbonylaminophenyl)-N',N'-dimethyl-acetamidine;
N-(cyclopentylcarbonylaminophenyl)-N',N'-dimethyl-acetamidine; hydrochloride, melting point 244°–247°;
N-(cyclohexylcarbonylaminophenyl)-N',N'-dimethyl-acetamidine;
N-(cycloheptylcarbonylaminophenyl)-N',N'-dimethyl-acetamidine;
N-(methylcyclopentylcarbonylaminophenyl)-N',N'-dimethyl-acetamidine;
N-(methyl-cyclohexylcarbonylaminophenyl)-N',N'-dimethyl-acetamidine;
N-(cyclopentenylcarbonylaminophenyl)-N',N'-dimethyl-acetamidine; and
N-(cyclohexenyl-1-carbonylaminophenyl)-N',N'-dimethyl-acetamidine hydrochloride, melting point 264°–268° (decomposition).

EXAMPLE 6

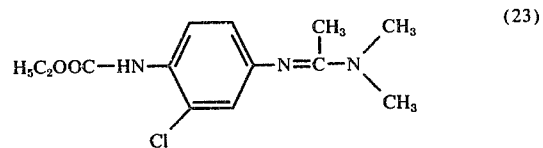

(23)

Following the method described in Example 1, 90 g of 4-carbethoxyamino-3-chloro-aniline, 46.6 g of N,N-dimethyl-acetamide and 79.5 g of phosphorus oxychloride in 100 ml of toluene yield 37 g of N-(4-carbethoxyamino-3-chlorophenyl)-N',N'-dimethyl-acetamidine, melting point 73° – 74°.

The following compounds are obtained by analogous processes:

(24)

| R' | R'' | R''' | R'''' | Melting point |
|---|---|---|---|---|
| 2-Cl | $CH_3$ | $CH_3$ | 4-$H_5C_2$OOC | HCl 212° decomposition |
| 2,5-$Cl_2$ | $CH_3$ | $CH_3$ | 4-$H_5C_2$OOC | |
| 2-$CH_3$ | $CH_3$ | $CH_3$ | 4-$H_5C_2$OOC | |
| 3-$CH_3$ | $CH_3$ | $CH_3$ | 4-$H_5C_2$OOC | |
| 2,6-$(CH_3)_2$ | $CH_3$ | $CH_3$ | 4-$H_5C_2$OOC | |
| 3-$C_2H_5$ | $CH_3$ | $CH_3$ | 4-$H_5C_2$OOC | |
| 3-CH—CH=$CH_2$ | $CH_3$ | $CH_3$ | 4-$H_5C_2$OOC | |
| 3-F | $CH_3$ | $CH_3$ | 4-$H_5C_2$OOC | |
| 2-Cl | $CH_3$ | $CH_3$ | 4-$CH_3$—CO | HCl 172–174° decomposition |
| 3-Cl | $CH_3$ | $CH_3$ | 4-$CH_3$—CO | |
| 3-$OCH_3$ | $CH_3$ | $CH_3$ | 4-$CH_3$—CO | |

-continued

|     | | | | (24) |
|---|---|---|---|---|

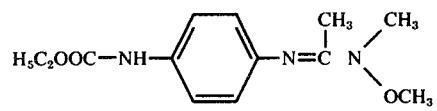

| R' | R'' | R''' | R'''' | Melting point |
|---|---|---|---|---|
| 3-Br | CH₃ | CH₃ | 4-CH₃—CO | |
| 3-CF₃ | CH₃ | CH₃ | 4-CH₃—CO | |
| 2-Cl | CH₃ | CH₃ | 4—CH₂=C—CO<br>    $\|$<br>    H₃C | HCl 252–253°<br>decomposition |
| 3-CN | CH₃ | CH₃ | 4-CH₃—CO | |
| 3-Cl | CH₃ | CH₃ | 4-C₂H₅—CO | |
| 2-Cl | CH₃ | CH₃ | 4-C₂H₅—CO | |
| 2-Cl | CH₃ | C₂H₅ | 4-CH₃—CO | |
| 3-Cl | CH₃ | C₂H₅ | 4-CH₃—CO | |
| 2-Cl | CH₃ | CH₃ | 4-C₆H₅—CO | HCl 290° |
| 2-CF₃ | CH₃ | CH₃ | 4-H₅—C₂OOC | |
| 2-CF₃ | CH₃ | CH₃ | 4-CH₃—CO | |

EXAMPLE 7

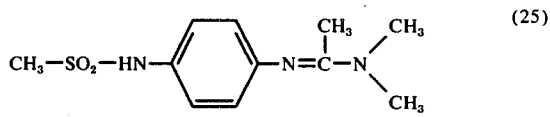
(25)

10.7 g of methanesulphonic acid chloride are added dropwise to 16.8 g of N-(4-aminophenyl)-N',N'-dimethyl-acetamidine in 300 ml of toluene, the mixture is stirred for a further hour, and the hydrochloride which has precipitated is filtered off and recrystallised from ethanol. 15.8 g of N-(4-methylsulphonyl-aminophenyl)-N',N'-dimethyl-acetamidine hydrochloride. melting point 273°. are obtained.

The following compounds are obtained by analogous processes:

N-(4-ethylsulphonylaminophenyl)-N'-N'-dimethyl-acetamidine, hydrochloride, melting point 246°–248°;

N-(4-propylsulphonylaminophenyl)-N',N'-dimethyl-acetamidine;

N-(4-isopropylsulphonylaminophenyl)-N',N'-dimethyl-acetamidine;

N-(4-butylsulphonylaminophenyl)-N',N'-dimethyl-acetamidine;

N-(4-isobutylsulphonylaminophenyl)-N',N'-dimethyl-acetamidine;

N-(4-hexylsulphonylaminophenyl)-N',N'-dimethyl-acetamidine;

N-(4-allylsulphonylaminophenyl)-N',N'-dimethyl-acetamidine;

N-(4-methallysulphonylaminophenyl)-N',N'-dimethyl-acetamidine;

N-(4-crotylsulphonylaminophenyl)-N',N'-dimethyl-acetamidine;

N-(4-cyclopropylsulphonylaminophenyl)-N',N'-dimethylacetamidine;

N-(4-cyclobutylsulphonylaminophenyl)-N',N'-dimethylacetamidine;

N-(4-cyclopentylsulphonylaminophenyl)-N',N'-dimethylacetamidine;

N-(4-cyclohexylsulphonylaminophenyl)-N',N'-dimethylacetamidine;

N-(4-cycloheptylsulphonylaminophenyl)-N',N'-dimethylacetamidine; and

N-(4-dodecylsulphonylaminophenyl)-N',N'-dimethylacetamidine.

EXAMPLE 8

13.6 g of chloroformic acid ethyl ester are added dropwise at 20° to 16.8 g of N-(4-aminophenyl)-N-methyl-N-methoxy-acetamidine in 200 ml of ethanol, the mixture is heated for one hour under reflux and evaporated in vacuo, and after recrystallisation from ethanol/ethyl acetate 22.1 g of N-(4-carbethoxyaminophenyl)-N'-methyl-N'-methoxy-acetamidine hydrochloride are obtained.

The N-(4-aminophenyl)-N'-methyl-N'-methoxyacetamidine used as the starting material is obtained in the following manner; p-nitroacetanilide is converted by means of phosphorus pentachloride into p-nitrophenyl-acetimide chloride, boiling point $_{0.5}$130° and this is reacted with N,O-dimethylhydroxylamine to give N-(4-aminophenyl)-N'-methyl-N'-methoxyacetamidine, boiling point $_{0.1}$150°, which is catalytically reduced to N-4-(aminophenyl)-N'-methyl-N'-methoxy acetamidine, boiling point $_{0.1}$154°–156°.

The following compounds are obtainable by processes analogous to that desired in Example 8:

N-(4-carbomethoxyaminophenyl)-N'-methyl-N'-methoxy-acetamidine;

N-(4-carbobutoxyaminophenyl)-N'-methyl-N'-methoxy-acetamidine;

N-(4-acetaminophenyl)-N'-methyl-N'-methoxy-acetamidine;

N-(4-propionaminophenyl)-N'-methyl-N'-methoxy-acetamidine;

N-(4-butyrylaminophenyl)-N'-methyl-N'-methoxy-acetamidine;

N-(4-methylsulphonylaminophenyl)-N'-methyl-N'-methoxy-acetamidine;

N-(4-ethylsulphonylaminophenyl)-N'-methyl-N'-methoxy-acetamidine;

N-(4-benzoylaminophenyl)-N'-methyl-N'-methoxy-acetamidine;

N-(4-phenylacetylaminophenyl)-N'-methyl-N'-methoxy-acetamidine;

N-(4-methoxyacetylaminophenyl)-N'-methyl-N'-methoxy-acetamidine;

N-[4-furylcarbonyl-(2)-aminophenyl]-N'-methyl-N'-methoxy-acetamidine;

N[4(4-chlorobenzoylamino)phenyl]-N'-methyl-N'-methoxy-acetamidine;

N'[4-(3-methylbenzoylamino)phenyl]-N'-methyl-N'-methoxy-acetamidine;

N-[4-(2-pyridylcarbonylamino)phenyl]-N'-methyl-N'-methoxy-acetamidine;

N-[4-(4-pyridylcarbonylamino)phenyl]-N'-methyl-N'-methoxy-acetamidine;

N-[4-(5-methylisoxyzolycarbonyl-[3]-amino)-phenyl]-N'-methyl- N'-methoxy-acetamidine;

N-(4-carbethoxyaminophenyl)-N'-ethyl-N'-methoxy-acetamidine;

N-(4-acetaminophenyl)-N'-ethyl-N'-methoxy-acetamidine;

N-(4-methylsulphonylaminophenyl)-N'-ethyl-N'-methoxyacetamidine;
N-(4-ethylsulphonylaminophenyl)-N'-ethyl-N'-methoxyacetamidine;
N-(4-carbethoxyaminophenyl)-N'-ethyl-N'-ethoxyacetamidine; and
N-(4-acetaminophenyl)-N'-ethyl-N'-ethoxyacetamidine.

EXAMPLE 9

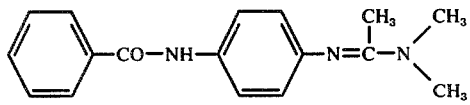 (27)

14.05 g of benzoyl chloride are added dropwise, at 20°, to 17.7 g of N-(4-aminophenyl)-N',N'-dimethylacetamidine in 150 ml of ethanol, and the mixture is heated for one hour under reflux. After cooling, the N-(4-benzoylaminophenyl)-N',N'-dimethyl-acetamidine hydrochloride which has separated out is filtered off; after recrystallisation from ethanol it has a melting point of 273°–274°; yield: 24.4 g. A further 3.5 g can be obtained from the mother liquor.

The following are obtained by analogous processes:
N[4-(4-chlorobenzoylamino)-phenyl]-N',N'-dimethylacetamidine;
N-[4-(3-chlorobenzoylamino)-phenyl]-N',N'-dimethylacetamidine;
N-[4-(2-chlorobenzoylamino)-phenyl]-N',N'-dimethylacetamidine;
N-[4-(4-methylbenzoylamino)-phenyl]N',N'-dimethylacetamidine;
N-[4-(3-methylbenzoylamino)-N',N'-dimethylacetamidine;
N-[4-(2-methylbenzoylamino)-phenyl]-N',N'-dimethylacetamidine;
N-[4-(2,6-dichlorobenzoylamino)-phenyl]-N',N'-dimethylacetamidine;
N-[4-(4-nitrobenzoylamino)-phenyl]-N',N'-dimethylacetamidine;
N-[4-(4-nitro-2-chlorobenzoylamino)-phenyl]-N',N'-dimethylacetamidine;
N-[4-(4-bromobenzoylamino)-phenyl]-N',N'-dimethylacetamidine;
N-[4-(2,4-dichlorobenzoylamino)-phenyl]-N',N'-dimethylacetamidine;
N-[4-(2,3-dichlorobenzoylamino)-phenyl]-N',N'-dimethylacetamidine;
N-[4-(3,4-dichlorobenzoylamino)-phenyl]-N',N'-dimethylacetamidine;
N-[4-(2,3,6-trichlorobenzoylamino)-phenyl]-N',N'-dimethylacetamidine;
N-[4-(4-fluorobenzoylamino)-phenyl]-N',N'-dimethylacetamidine;
N-[4-(3-trifluoromethylbenzoylamino)-phenyl]-N',N'-dimethylacetamidine;
N-[4-(3-chloro-6-acetyloxybenzoylamino)-phenyl]-N',N'-dimethylacetamidine, hydrochloride, melting point 292°–295°;
N-[4-(4-methoxybenzoylamino)phenyl]-N',N'-dimethylacetamidine; N-[4-(3-methoxybenzoylamino)phenyl]-N',N'-dimethylacetamidine;
N-[4-(2-methoxybenzolamino)phenyl]-N',N'-dimethylacetamidine;
N-[4-(3-chloro-6-methoxybenzoylamino)phenyl]-N',N'-dimethylacetamidine;
N-[4-(2-chloro-4-methoxybenzoylamino)phenyl]-N',N'-dimethylacetamidine;
N-[4-(2,3-dimethoxybenzoylamino)phenyl]-N',N'-dimethylacetamidine;
N-[4-(3-carbethoxyamino-4-methoxybenzoylamino)phenyl]-N',N'-dimethylacetamidine;
N-[4-(4-acetylamino-methoxybenzoylamino)-phenyl]-N',N'-dimethylacetamidine;
N-[4-(3-butoxybenzoylamino)phenyl]-N',N'-dimethylacetamidine;
N-[4-(4-(4-ethoxybenzoylamino)phenyl]-N',N'-dimethylacetamidine;
N-[4-(3,4,5-trimethoxybenzoylamino)phenyl]-N',N'-dimethylacetamidine;
N-[4-(4-methylsulphonylbenzoylamino)phenyl]-N',N'-dimethylacetamidine;
N-[4-(2-methylsulphonylbenzoylamino)phenyl]-N',N'-dimethylacetamidine;
N-[4-(3,4-dimethylbenzoylamino)phenyl]-N',N'-dimethylacetamidine;
N-[4-(2-methylsulphonylaminobenzoylamino)phenyl]-N',N'-dimethylacetamidine;
N-(4-(phenoxyacetylaminophenyl)-N',N'-dimethylacetamidine, hydrochloride, melting point 256°–257° (decomposition);
N-(4-(2-phenoxypropionylaminophenyl)-N',N'-dimethylacetamidine;
N-(4-(2-phenoxybutyrylaminophenyl)-N',N'-dimethylacetamidine;
N-[4-(methylphenoxy)-acetylaminophenyl]-N',N'-dimethylacetamidine;
N-[4-(2-methoxyphenoxy)-acetylaminophenyl]-N',N'-dimethylacetamidine;
N-[4-(2-isopropylphenoxy)-acetylaminophenyl]-N',N'-dimethylacetamidine;
N-[4-(3,4-dimethylphenoxy)-acetylaminophenyl]-N',N'-dimethylacetamidine;
N-[4-(3,5-dimethoxyphenoxy)-acetylaminophenyl]-N',N'-dimethylacetamidine;
N-[4-(2-chlorophenoxy)-acetylaminophenyl]-N',N'-dimethylacetamidine;
N-[4-(2-methyl-4-chlorophenoxy)acetylaminophenyl]-N',N'-dimethylacetamidine;
N-[4-(2,4-dichlorophenoxyacetylamino-phenyl-]-N',N'-dimethylacetamidine;
N-[4-(2,5-dichlorophenoxy)acetylamino-phenyl]-N',N'-dimethylacetamidine;
N-[4-(4-nitrophenoxy)acetaminophenyl]-N',N'-dimethylacetamidine;
N-(4-cinnamoylaminophenyl)-N',N'-dimethylacetamidine, hydrochloride, melting point 280°–285° (decomposition);
N-[4-(2,6-dichlorocinnamoylamino)phenyl]-N',N'-dimethylacetamidine;
N-[4-(1-naphthoylaminophenyl)]-N',N'-dimethylacetamidine; N-[4-(2-naphthoylaminophenyl)]-N',N'-dimethylacetamidine;
N-[4-(2-indenylcarbonylaminophenyl)]-N',N'-dimethylacetamidine;
N-[4-(1-indenylcarbonylaminophenyl)]-N',N'-dimethylacetamidine;
N-[4-(1-tetralylcarbonylaminophenyl)]-N',N'-dimethylacetamidine;
N-[4-(2-tetralylcarbonylaminophenyl)]-N',N'-dimethylacetamidine;

N-[4-(5-tetralylcarbonylaminophenyl)]-N',N'-dimethylacetamidine;

N-[4-(2-hydroxybenzoylamino)phenyl]-N',N'-dimethylacetamidine;

N-[4-82-hydroxy-4-chlorobenzoylamino)phenyl]-N',N'-dimethylacetamidine;

N-[4-(2-hydroxy-3,5-dichlorobenzoylamino)-phenyl]-N',N'-dimethylacetamidine;

N-[4-(2-acetoxy-3,5-dichlorobenzoylamino)-phenyl]-N',N'-dimethylacetamidine;

N-[4-(2-acetoxy-3-bromo-5-chlorobenzoylamino)-phenyl]-N',N'-dimethylacetamidine; and N-[4-(2-hydroxy-3,5,6-trichlorobenzoylamino)-phenyl]-N',N'-dimethylacetamidine.

EXAMPLE 10

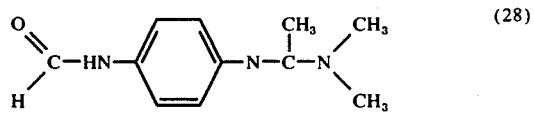 (28)

A solution of 17.7 g of N-(4-aminophenyl)-N',N'-dimethyl-acetamidine in 150 ml of benzene is heated with 50 ml of formic acid ethyl ester for 4 hours under reflux. The mixture is evaporated; after distillation in vacuo 18.7 g of N-(4-formylaminophenyl)-N',N'-dimethylacetamidine, boiling point $_{0.1}185°-188°$, are obtained; hydrochloride: melting point 279°–281°.

EXAMPLE 11

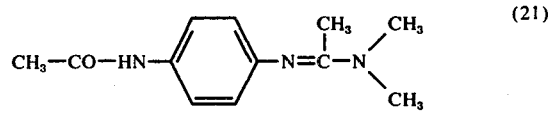 (21)

17.7 g of N-(4-aminophenyl)-N',N'-dimethylacetamidine in 100 ml of acetic anhydride are heated for 4 hours under reflux, the mixture is evaporated, the residue is rendered alkaline with sodium hydroxide solution, and the organic phase is taken up in chloroform/ether and distilled in vacuo. 14.8 g of N-(4-acetaminophenyl)-N',N'-dimethyl-acetamidine, melting point 132°–134°, are obtained.

EXAMPLE 12

96 g of 4-acetaminoacetanilide in 300 ml of toluene are stirred with 76 g of phosphorus oxychloride for 6 hours at 20°. A solution of 60 g of dimethylamine in 200 ml of toluene is then added dropwise and the mixture is heated overnight under reflux. After working up as described in Example 1, 27 g of N-(4-acetaminophenyl)-N',N'-dimethylacetamidine, boiling point $_{0.1}190°-200°$, are obtained, melting at 131°–134° after recrystallisation.

EXAMPLE 13

A solution of 51.5 g of N,N-dimethylthioacetamide and 74 g of p-aminoacetanilide in 500 ml of ethanol, with 185 g of mercury oxide added, is vigorously stirred for 8 hours at 0° and then for 15 hours at 80°. The precipitate is filtered off, the residue is distilled in vacuo, and 24.6 g of N-(4-acetaminophenyl)-N',N'-dimethyl-acetamidine, boiling point $_{0.1}190°-200°$, melting point 131°–134°, are obtained.

The same compound is also obtained from 4-acetaminothioacetanilide and dimethylamine in the presence of mercury oxide, by an analogous process.

EXAMPLE 14

50 ml of dimethylacetamide and 25 g of p-acetaminophenylisocyanate are heated under reflux until the evolution of $CO_2$ has ceased. The reaction product is distilled in vacuo, and 7.5 g of N-(4-acetaminophenyl)-N',N'-dimethylacetamidine, boiling point $_{0.1}180°-200°$, melting point 131°–134°, are obtained.

The same compound is also obtained by heating 4-acetamino-phenylcarbamine acid chloride and with dimethylacetamide or dimethylthioacetamide.

EXAMPLE 15

98 g of 4-acetaminophenyl-acetiminoethyl-ether in a solution of 26 g of dimethylamine in 100 ml of ethanol are heated for two days to 28° and then for 6 hours in a sealed tube to 120°–130°. After evaporation and distillation, 57 g of N-(4-acetaminophenyl)-N',N'-dimethylacetamidine, melting point 131°–134°, are obtained. Correspondingly, reaction of 4-acetiminophenyl-acetiminoethyl-ether with ammonia yields N-(4-acetaminophenyl)-acetamidine. The same compound is also produced by reaction of 4-aminoacetanilide with acetiminoethyl-ether.

EXAMPLE 16 PRODUCTION OF A STARTING MATERIAL FOR USE IN A PROCESS OF THE INVENTION 140 g of p-amino-acetanilide and 36 g of acetonitrile in 400 ml of carbon disulphide are treated with 144 g of aluminium chloride over the course of 1 hour. The solvent is then distilled off, and the reaction mixture is heated for 4 hours to 150°–160°. Thereafter it is poured onto a mixture of ice and water, the whole is filtered, the filtrate is rendered alkaline with saturated potassium carbonate solution, and the oil which has separated out is taken up in ether. After evaporating off the solvent, 33 g of N-(4-acetaminophenyl)-acetamidine are obtained. Boiling point $_{0.3}173°-176°$.

EXAMPLE 17

11 g of sodium carbonate are added to a solution of 38.2 g of N-(4-acetaminophenyl)-acetamidine as produced in Example 16 in 200 ml of tetrahydrofurane, and 57 g of methyl iodide are added dropwise. The mixture is heated overnight under reflux, inorganic constituents which have separated out are filtered off, the filtrate is concentrated in vacuo, and the residue is taken up in water and rendered alkaline with sodium hydroxide solution. The separated base is taken up in a mixture of ether/chloroform, which is evaporated, and is distilled. After recrystallisation from ethyl acetate, 17.8 g of N-(4-acetaminophenyl)-N',N'-dimethylacetamidine of melting point 131°–134° are obtained.

The following are obtained by analogous processes:
N-(4-acetaminophenyl)-N'-allyl-acetamidine;
N-(4-acetaminophenyl)-N'-methallyl-acetamidine;
N-(4-acetaminophenyl)-N'-crotyl-acetamidine;
N-(4-propionylaminophenyl)-N'-allyl-acetamidine;
N-(4-propionylaminophenyl)-N'-methallyl-acetamidine; N-(4-carbethoxyaminophenyl)-N'-allyl-acetamidine;
N-(4-carbethoxyaminophenyl)-N'-crotyl-acetamidine;

N-(4-methanesulphonylaminophenyl)-N'-allyl-acetamidine;

N-(4-carbethoxyaminophenyl)-N',N'-diallyl-acetamidine; N-(4-acetaminophenyl)-N'-N'-diallyl-acetamidine; N-(4-propionaminophenyl)-N',N'-diallyl-acetamidine; N-(4-methylsulhonylaminophenyl)-N',N'-diallyl-acetamidine; and N-(4-acetaminophenyl)-N',N'-dicrotyl-acetamidine.

EXAMPLE 18

Following the method described in Example 17, alkylation of N-(4-acetaminophenyl)-N'-methylacetamidine with allyl chloride in the presence of potassium carbonate yields N-(4-acetaminophenyl)-N'-allyl-N'-methyl-acetamidine.

The following are obtained by proceeding analogously: N-(4-acetaminophenyl)-N'-methyl-N'-crotyl-acetamidine; N-(4-acetaminophenyl)-N'-methyl-N'-methallyl-acetamidine;

N-(4-acetaminophenyl)-N'-methyl-N'-propynyl-acetamidine;

N-(4-acetaminophenyl)-N'-methyl-N'-butynyl-(2)-acetamidine;

N-(4-propionaminophenyl)-N'-methyl-N'-allyl-acetamidine;

N-(4-propionaminophenyl)-N'-methyl-N'-crotyl-acetamidine;

N-(4-propionaminophenyl)-N'-ethyl-N'-allyl-acetamidine;

N-(4-carbethoxyaminophenyl)-N'-methyl-N'-allyl-acetamidine;

N-(4-carbethoxyaminophenyl)-N'-methyl-N-butynyl-(2)-acetamidine;

N-(4-carbethoxyaminophenyl)-N'-ethyl-N'-allyl-acetamidine;

N-(4-methylsulphonylaminophenyl)-N'-methyl-N'-allyl-acetamidine;

N-(4-methylsulphonylaminophenyl)-N'-methyl-N'-crotyl-acetamidine;

N-(4-methylsulphonylaminophenyl)-N'-methyl-N'-propynyl-acetamidine; and

N-(4-ethylsulphonylaminophenyl)-N'-methyl-N'-allyl-acetamidine;

EXAMPLE 19

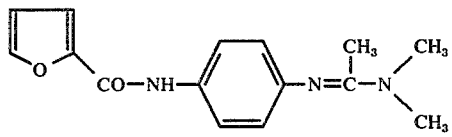
(29)

Following the method described in Example 9, 17.7 g of N-(4-aminophenyl)-N',N'-dimethylacetamidine and 15.7 g of 2-furanecarboxylic acid chloride in ethanol yield 27.7 g of N-[4-(2-furylcarbonylamino)phenyl]-N',N'-dimethyl-acetamidine hydrochloride, melting point 270°–272°.

The following are obtained by analogous processes:
N-[4-(5-methylisoxazolylcarbonyl-[3]-amino)-phenyl]-N',N'-dimethylacetamidine, hydrochloride, melting point 308°–309°, decomposition;

N-[4-(2-pyridylcarbonylamino)phenyl]-N',N'-dimethylacetamidine;

N-[4-(3-pyridylcarbonylamino)phenyl]-N',N'-dimethylacetamidine;

N-[4-(4-pyridylcarbonylamino)phenyl]-N',N'-dimethylacetamidine;

N-[4-(2-thienylcarbonylamino)phenyl]-N',N'-dimethylacetamidine;

N-[4-(2-furfurylcarbonylamino)phenyl]-N',N'-dimethylacetamidine;

N-[4-(2-indolylcarbonylamino)phenyl]-N',N'-dimethylacetamidine;

N-[4-(2-thianaphthylcarbonylamino)phenyl]-N',N'-dimethylacetamidine;

N-[4-(3-indolylacetylamino)phenyl]-N',N'-dimethylacetamidine;

N-[4-(3-quinolylcarbonylamino)phenyl]-N',N'-dimethylacetamidine;

N-[4-(2-phenothiazinylcarbonylamino)phenyl]-N',N'-dimethylacetamidine;

N-[4-(2-thienylacetylamino)phenyl]-N',N'-dimethylacetamidine;

N-[4-(3-pyrazolylcarbonylamino)phenyl]-N',N'-dimethylacetamidine;

N-[4-(4-methyl-3-pyrazolylcarbonylamino)phenyl]-N',N'-dimethyl-acetamidine;

N-[4-(2-imidazolylcarbonylamino)phenyl]-N',N'-dimethylacetamidine;

N-[4-pyrazinylcarbonyl-aminophenyl]-N',N'-dimethylacetamidine;

N-[4-(4-pyrimidinylcarbonylamino)phenyl]-N',N'-dimethylacetamidine; and

N-[4-(5-thiazolylcarbonylamino)phenyl-N',N'-dimethylacetamidine.

As already mentioned, the new aminophenylamidines and salts are suitable for combating parasites, especially helminths.

It is distinctyl surprising and unforeseeable that a high anthelmintic activity should arise as a result of the introduction of an acylamino or of a sulphonylamino group into the phenyl nucleus of the N-phenylacetamidines. Furthermore, the new compounds have a substantially better action than other known anthelmintics having the same type of action, such as, for example, bephenium hydroxynaphthoates, phenylene-1,4-diisothiocyanate, perchloroethylene, thiabendazole and parbendazole. Particular attention is drawn to the fact that excellent results are achieved with a single dose.

The provision by the invention of the new compounds available extends substantially the range of available medicines.

In particular, the compounds manufactured according to the invention for example display a surprisingly good and broad action against the following helminths (nematodes and cestodes):

I. Nematodes

1. *Ancylostoma canium, Uncinaria stenocephala* and *Bunostromun trigonocephalum* (hookworms) from the family of the *Ancylostomatidae;*

2. *Haemonchus contortus, Trichostrongylus colubriformis, Cooperia punctata, Ostertagia circumcincta, Nippostrongylus musis* and *Nematospiroides dubius* (worms of the stomach and of the small intestine) from the family of the *Trichostrongylidae;*

3. *Oesophagostomum columbianum* and *Chabertia ovina* (worms of the large intestine) from the family of the *Stronglylidae;*

4. *Strongyloides ratti* (dwarf threadworms) from the family of the *Rhabditidae;*

5. *Toxocara canis, Toxascaris leonina* and *Ascaris suum* larvae (coilworms) from the family of the *Ascarididae.*

6. *Aspiculuris tetraptera* (maggot worms) from the family of the *Oxyuridae*;

7. *Heterakis spumosa* from the family of the *Heterakidae*.

II. Cestodes

1. *Hymenolepis nana* and *Hymenolepis microstoma* (tapeworms) from the super-family of the *Taenioidea*.

The action was tested in animal experiments, by oral and parenteral administration to test animals severely infected with parasites. The doses used were tolerated very well by the test animals. Even at 10 to 100 times the therapeutically necessary dose, the test animals survived the treatments.

The unexpected superiority of the compounds according to the invention over known compounds, as well as the excellent action against a multiplicity of parasites, is shown by the Examples A to G (Tables 1–7).

EXAMPLE A

Hookworm test/dog

Dogs experimentally infected with *Ancylostome canium* were treated after the end of the pre-patent period of the parasites.

The amount of active compound was administered orally as the pure active compound or as a 10% strength solution in lactic acid, in gelatine capsules.

The degree of action was determined by counting the worms expelled after the treatment and the worms remaining in the test animal, after dissection, and calculating the percentage of worms expelled.

The active compounds tested, doses used and action are summarised in Table 1 below.

Table 1

Hookworm test/dog

| Active compounds | | Dose mg/kg | Action in % |
|---|---|---|---|
| known compounds: | | | |
| $CH_3-CO-NH-\langle\bigcirc\rangle-N=CH-N(CH_3)_2$ | (30) | 50 | 0 |
| $Cl-\langle\bigcirc\rangle-N=C(CH_3)-N(CH_3)_2$ | (31) | 25 | 0 |
| $Cl-C(Cl)=C(Cl)-Cl$ | (32) | 300 | 82 |
| $S=C=N-\langle\bigcirc\rangle-N=C=S$ | (33) | 50 | 51 |
| $[C_6H_5-O-(CH_2)_2-N(CH_3)_2-CH_2-C_6H_5]^+$ | *) | 60 | 46 |
| naphthalene-COO⁻/OH (Bephenium hydroxynaphthoate) | (34) | 100 | 65 |
| n-$H_9C_4$-benzimidazole-NH-C(O)-OCH$_3$ (Parbendazole) | **) (35) | 100 200 | 77 93 |

*) Literature:
Rawes, D.A. (1961): The Activity of Bephenium Hydroxynaphthoate against Hookworms in the Dog. Vet. Rec. 73 (16), 390–392

**) Literature:
Theodorides, V.J. and M. Laderman (1968): Parbendazole in the Treatment of Intestinal Nematodes of Dogs and Monkeys. Vet. Med. 63 (10), 985.

| | | | |
|---|---|---|---|
| benzimidazole-thiazoline (Tetramisole) | (36) | 100 | 0 |
| compounds according to the invention: | | | |
| $H_5C_2OOC-HN-\langle\bigcirc\rangle-N=C(CH_3)-N(CH_3)_2$ | (19) | 5 10 25 | 88 85 100 |

Table 1-continued

Hookworm test/dog

| Active compounds | | Dose mg/kg | Action in % |
|---|---|---|---|
| H₅C₂OOC—HN—C₆H₄—N=C(CH₃)—N(CH₃)₂ · HCl | (37) | 2.5 / 5.0 / 10.0 | 98 / 98 / 100 |
| H₉C₄OOC—C₆H₄—N=C(C₃)—N(CH₃)₂ · HCl | (20) | 5 / 10 | 60 / 95 |
| H₃CCO—HN—C₆H₄—N=C(CH₃)—N(CH₃)(CH₃) | (21) | 5 / 10 | 64 / 100 |
| H₅C₂OC—HN—C₆H₄—N=C(CH₃)—N(CH₃)₂ · HCl | (38) | 25 | 92 |
| CH₃O—CH₂—CO—NH—C₆H₄—N=C(CH₃)—N(CH₃)₂ | (39) | 5 / 10 / 25 | 65 / 77 / 100 |
| C₆H₅—CO—NH—C₆H₄—N=C(CH₃)—N(CH₃)₂ · HCl | (27) | 10 | 84 |
| CH₃—SO₂—NH—C₆H₄—N=C(CH₃)—N(CH₃)₂ · HCl | (25) | 25 | 80 |
| C₂H₅—SO₂—NH—C₆H₄—N=C(CH₃)—N(CH₃)₂ · HCl | (40) | 10 / 25 | 47 / 100 |
| HC≡C—H₂COOC—HN—C₆H₄—N=C(CH₃)—N(CH₃)₂ | (41) | 5 | 76 |
| CH₃—CH₂—CH₂OOC—HN—C₆H₄—N=C(CH₃)—N(CH₃)₂ · HCl | (42) | 10 | 82 |
| H₃CO—CH₂—CH₂OOC—HN—C₆H₄—N=C(CH₃)—N(CH₃)₂ | (43) | 10 | 63 |
| OHC—HN—C₆H₄—N=C(CH₃)—N(CH₃)₂ · HCl | (44) | 5 | 100 |
| F₃C—OC—HN—C₆H₄—N=C(CH₃)—N(CH₃)₂ · HCl | (45) | 10 | 100 |
| 2-furyl—CO—HN—C₆H₄—N=C(CH₃)—N(CH₃)₂ · HCl | (29) | 25 | 98 |
| 3-methyl-isoxazol-5-yl—CO—HN—C₆H₄—N=C(CH₃)—N(CH₃)₂ · HCl | (46) | 10 | 100 |

Table 1-continued

| Active compounds | | Dose mg/kg | Action in % |
|---|---|---|---|
| $H_5C_2OOC-HN-\langle\text{aryl-Cl}\rangle-N=C(CH_3)-N(CH_3)_2 \cdot HCl$ (47) | | 10 | 96 |

EXAMPLE B

Hookworm test/dog

Dogs experimentally infected with *Uncinaria stenocephala* were treated after the end of the pre-patent period of the parasites.

The amount of active compound was administered orally as the pure active compound or as a 10% strength solution in lactic acid, in gelatine capsules.

The degree of action was determined by counting the worms expelled afte the treatment and the worms remaining in the test animal, after dissection, and calculating the percentage of worms expelled.

The active compounds tested, doses used and action are summarised in Table 2 below.

Table 2

| Active compounds | | Dose mg/kg | Action in % |
|---|---|---|---|
| $H_5C_2OOC-NH-\langle\text{aryl}\rangle-N=C(CH_3)-N(CH_3)_2$ | (19) | 10<br>5 | 92<br>92 |
| $H_7C_3OOC-NH-\langle\text{aryl}\rangle-N=C(CH_3)-N(CH_3)_2$ | (48) | 5<br>2.5 | 99<br>42 |
| $H_9C_4OOC-NH-\langle\text{aryl}\rangle-N=C(CH_3)-N(CH_3)_2$ | (49) | 10 | 89 |

EXAMPLE C

Hookworm test/dog

Dogs experimentally infected with *Ancylostoma caninum* were treated after the end of the pre-patent period of the parasites.

The amount of active compound was administered subcutaneously as a 1% strength solution in distilled water.

The degree of action was determined by counting the worms expelled after the treatment and the worms remaining in the test animal, after dissection, and calculating the percentage of worms expelled.

The active compound tested, dose used and action are summarised in Table 3 below.

Table 3:

| Active compound | | Dose mg/kg | Action in % |
|---|---|---|---|
| $H_5C_2OOC-NH-\langle\text{aryl}\rangle-N=C(CH_3)-N(CH_3)_2 \cdot HCl$ | (50) | 5 | 99 |

EXAMPLE D

Hookworm test/sheep

Sheep experimentally infected with *Bunostomum trigonocephalum* were treated after the end of the pre-patent period of the parasites.

The amount of active compound was administered orally as pure active compound in gelatine capsules.

The degree of action is determined by counting the worms expelled after the treatment and the worms remaining in the test animals, after dissection, and calculating the percentage of worms expelled.

The active compounds tested, doses used and action are summarised in Table 4 below.

Table 4:

| Hookworm test/sheep | | Dose mg/kg | Action in % |
|---|---|---|---|
| Active compound | | | |
| $H_5C_2OOC-NH-\langle\text{phenyl}\rangle-N=C(CH_3)-N(CH_3)_2$ | (19) | 1.0<br>2.5<br>5.0 | 95<br>98<br>100 |
| $H_5C_2OOC-NH-\langle\text{phenyl}\rangle-N=C(CH_3)-N(CH_3)_2 \cdot HCl$ | (50) | 1.0<br>5.0 | 92<br>98 |
| $H_3COOC-NH-\langle\text{phenyl}\rangle-N=C(CH_3)-N(CH_3)_2$ | (51) | 10 | 100 |

EXAMPLE E

Stomach and intestine worm test/sheep

Sheep experimentally infected with *Haemonchus contortus* and *Trichostrongylus colubriformis* were treated after the end of the pre-patent period of the parasites.

The amount of active compound was administered orally as pure active compound, in gelatine capsules.

The degree of action is determined by quantitatively counting the worm eggs excreted with the faeces before and after treatment.

Complete cessation of the excretion of eggs after treatment means that the means have been expelled or so damaged that they can no longer produce eggs (effective dose).

The active compound tested and the minimum effective dose is shown in Table 5.

Table 5:

| Stomach and intestine worm test/sheep | | Minimum effective dose mg/kg |
|---|---|---|
| Active compound | Parasite | |
| $H_5C_2OOC-NH-\langle\text{phenyl}\rangle-N=C(CH_3)-N(CH_3)_2$ (19) | Haemonchus contortus | 10 |
|  | Trichostr. colubriformis | 25 |

EXAMPLE F

Large-intestine worm test/sheep

Sheep experimentally infected with *Oesophagostomum columbianum* were treated after the end of the pre-patent period of the parasites.

The amount of active compound was administered orally as pure active compound in gelatine capsules.

The degree of action is determined by counting the worms expelled after the treatment and the worms remaining in the test animals, after dissection, and calculating the percentage of worms expelled.

The active compounds tested, doses used and action are shown in Table 6 below.

Table 6:

| Large-intestine worm test/sheep | | Dose mg/kg | Action in % |
|---|---|---|---|
| Active compounds | | | |
| $H_5C_2OOC-NH-\langle\text{phenyl}\rangle-N=C(CH_3)-N(CH_3)_2$ | (19) | 1.0<br>5.0<br>10.0 | 65<br>100<br>100 |
| $H_5C_2OOC-NH-\langle\text{phenyl}\rangle-N=C(CH_3)-N(CH_3)_2 \cdot HCl$ | (50) | 1.0 | 76 |

EXAMPLE G

Coilworm test/dog

Dogs naturally infected with *Toxocara canis* and *Toxascaris leonina* were treated orally.

The amount of active compound was administered orally as pure active compound or as a 10% strength solution in lactic acid, in gelatine capsules.

The degree of action is determined by counting the worms expelled after the treatment and the worms remaining in the test animals, after dissection, and calculating the percentage of worms expelled.

The active compounds tested, doses used and action are summarised in Table 7 below.

Table 7:

| Active compounds | | Parasite | Dose mg/kg | Action in % |
|---|---|---|---|---|
| H₂C₂OOC—NH—C₆H₄—N=C(CH₃)—N(CH₃)₂ | (19) | Toxocara | 10 | 86 |
| H₅C₂OOC—NH—C₆H₄—N=C(CH₃)—N(CH₃)₂ · HCl | (50) | Toxocara | 2.5 | 100 |
| | | Toxascaris | 5.0 | 83 |
| H₉C₄OOC—NH—C₆H₄—N=C(CH₃)—N(CH₃)₂ · HCl | (20) | Toxocara | 5 | 100 |
| | | | 25 | 100 |
| CH₃O—CH₂—CO—HN—C₆H₄—N=C(CH₃)—N(CH₃)₂ · HCl | (52) | Toxascaris | 10 | 75 |
| C₆H₅—CO—HN—C₆H₄—N=C(CH₃)—N(CH₃)₂ · HCl | (27) | Toxascaris | 25 | 98 |
| H₅C₂—SO₂—HN—C₆H₄—N=C(CH₃)—N(CH₃)₂ · HCl | (53) | Toxocara | 25 | 100 |
| HC≡C—H₂COOC—NH—C₆H₄—N=C(CH₃)—N(CH₃)₂ · HCl | (41) | Toxocara | 10 | 100 |
| CH₃—CH₂—CH₂—OOC—HN—C₆H₄—N=C(CH₃)—N(CH₃)₂ · HCl | (42) | Toxocara | 10 | 100 |
| | | Toxascaris | 5 | 75 |
| (H₃C)₂HC—CO—HN—C₆H₄—N=C(CH₃)—N(CH₃)₂ · HCl | (54) | Toxocara | 25 | 100 |
| C₆H₅—CO—HN—C₆H₄—N=C(CH₃)—N(CH₃)₂ · HCl | (27) | Toxascaris | 25 | 98 |
| OHC—HN—C₆H₄—N=C(CH₃)—N(CH₃)₂ · HCl | (44) | Toxocara | 25 | 100 |
| (3-methylisoxazol-5-yl)—CO—HN—C₆H₄—N=C(CH₃)—N(CH₃)₂ · HCl | (46) | Toxocara | 10 | 100 |
| H₃CCO—NH—C₆H₄—N=C(CH₃)—N(CH₃)₂ | (21) | Toxocara | 10 | 83 |

In general it has proved advantageous to administer amounts of about 0.1 to about 50 mg of the new compounds per kg of body weight per day in order to achieve effective results.

Nevertheless, it may at times be necessary to deviate from the amounts mentioned, and in particular to do so as a function of the body weight of the test animal or of the nature of the method of administration, but also because of the variety of animal and its individual behaviour towards the medicament or because of the nature of the formulation of the latter and the point in time, or interval, at which it is administered. Thus, it may in some cases suffice to use less than the above-mentioned minimum amount, whilst in other cases the upper limit mentioned must be exceeded. Where major amounts are administered, it may be advisable to divide these into several individual administrations over the course of a day. The same dosage range is envisaged for administration in human medicine and in veterinary medicine. The general sense of the other comments made above also applies.

As stated above, the invention relates to the pharmaceutical use, including the veterinary use, of the new aminophenylamidines and their non-toxic salts.

Accordingly, the present invention provides a pharmaceutical composition containing as an active ingredient at least one of the new aminophenylamidines of the general formula (1) given above, or a non-toxic salt thereof, in admixture with a pharmaceutically acceptable solid or liquid diluent or carrier as hereinafter defined.

In the present specification the expression "pharmaceutically acceptable diluent or carrier" means a non-toxic substance that when mixed with the active ingredient or ingredients renders it suitable for administration. The expression preferably excludes water and low-molecular weight organic solvents commonly used in chemical synthesis, except in the presence of other pharmaceutically necessary ingredients such as salts in correct quantities to render the composition isotonic, buffers, surfactants, colouring and flavouring agents, and preservatives. Examples of suitable solid and liquid diluents and carriers are the following: water containing buffering agents and/or rendered isotonic by the addition of glucose or salts; non-toxic organic solvents; such as paraffins, (for example petroleum fractions); vegetable oils (for example groundnut/sesame oil); alcohols, (for example ethyl alcohol or glycerol); glycols (for example propylene glycol or polyethylene glycol); natural ground rock (for example kaolins, aluminas, talc or chalk); synthetic rock powders (for example highly disperse silica or silicates); and sugars (for example unrefined sugar, lactose and glucose).

Examples of pharmaceutical compositions according to the invention are ointments, pastes, creams, sprays, lotions, aqueous suspensions, elixirs, syrups, granules and powders, either free-flowing or compressed into tablets.

The compounds and pharmaceutically acceptable salts of the present invention may be administered perorally.

One group of preferred pharmaceutical compositions of the invention are therefore those adapted for oral administration. The diluents and carriers used are preferably therefore those that adapt the active ingredient or ingredients for oral administration. Examples of such diluents and carriers are solid vehicles, excipients and lubricants such as glucose, lactose and sucrose, corn and potato starch, sodium carboxymethyl cellulose, ethyl cellulose and cellulose acetate, powdered gun tragacanth, gelatin, alginic acid, agar, stearic acid, sodium, calcium and magnesium stearates, sodium lauryl sulphate, polyvinyl-pyrrolidone, sodium citrate, calcium carbonate, and dicalcium phosphate.

The pharmaceutical compositions of the invention may also contain other non-toxic adjuvants and modifiers such as dyes, surfactants for example, emulsifiers, such as non-ionic and anionic emulsifiers (for example polyoxyethylene-fatty acid esters, polyoxyethylene-fatty alcohol ethers, alkylsulphonates and arylsulphonates), and dispersing agents (for example lignin, sulphite waste lyes, methylcellulose, starch and polyvinyl-pyrrolidone), perfumes, flavouring agents, preservatives and biocides.

The compounds and pharmaceutically acceptable salts of the invention may also be administered parenterally, in particular, subcutaneously. A group of preferred pharmaceutical compositions of the invention are therefore those adapted for parenteral injection. The diluents and carriers used here are therefore preferably those that adapt the active ingredient for parenteral adminisration. Examples of such diluents and carriers are solvents and suspending diluents such as water and water-miscible organic solvents, in particular sesame oil, groundnut oil, aqueous propylene glycol, and N,N'-dimethyl formamide. Examples of pharmaceutical compositions of the invention are sterile isotonic saline aqueous solutions of the active ingredients, which may be buffered with a pharmaceutically acceptable buffer and are preferably pyrogen-free.

The pharmaceutical compositions of the invention preferably contain 0.1 to 90 wt.% of a new aminophenylamidine of the invention or a non-toxic salt thereof.

The present invention also provides medicaments in dosage unit form as hereinafter defined comprising as an active ingredient at least one aminophenylamidine of general formula (1) given above or a non-toxic salt thereof, either alone or in admixture with a pharmaceutically acceptable solid or liquid diluent or carrier. In this case the diluent or carrier is preferably as defined above but can also be water or another common solvent.

The expression "medicament in dosage unit form" as used in the present specification means a medicament in the form of discrete portions each containing a unit dose or a multiple or sub-multiple of a unit dose of the active ingredient(s); for example, one, two, three, or four unit doses or a half, a third or a quarter of a unit dose. A "unit dose" is the amount of the active ingredient(s) to be administered on one occasion and will usually be a daily dose, or for example a half, a third, or a quarter of a daily dose depending on whether the medicament is to be administered once or, for example, twice, three times, or four times a day.

The discrete portions constituting the medicament in dosage unit form can include a protective envelope. The active ingredient can be undiluted and contained in such an envelope, or can be mixed with a pharmaceutically acceptable solid or liquid diluent or carrier as defined above. Such portions can for example be in monolithic coherent form, such as tablets, lozenges, pills, suppositories, or dragees; in wrapped or concealed form, the active ingredients being within a protective envelope, such as wrapped powders, cachets, sachets, capsules, or ampoules; or in the form of a sterile solution suitable for parenteral injection, such as ampoules of buffered, isotonic, sterile, pyrogen-free aqueous solution; or in any other form known in the art.

As stated above, it is preferred to administer the new aminophenylamidines of general formula (1) or their salts perorally. Preferred medicaments in dosage unit form according to the invention are therefore those adapted for oral administration, such as tablets, pills, dragees, capsules, and cachets, as well as wrapped powders containing the active ingredients in powdered form with a powdered diluent or carrier for suspension in water before being taken.

As stated above the new aminophenylcycloamidines can also be administered parenterally. Preferred medicaments in dosage unit form according to the invention are therefore those adapted for parenteral injection, such as ampoules containing a measured quantity of a sterile isotonic saline injectable aqueous solution of the new active ingredient, which may be buffered with a pharmaceutically acceptable buffer and are preferably free of pyrogens.

The preferred unit dose for administration in human medicine of the medicaments of the invention is 5–4500 mg. more preferably 50–2250 mg of active ingredient.

The invention further provides a method of combating parasitic infection in an animal which comprises administering to the animal (preferably parenterally or perorally) an aminophenylamidine of general formula (1) or a non-toxic salt thereof, or a pharmaceutical composition according to the invention, or a medicament in dosage unit form according to the invention.

What we claim is:

1. A compound selected from the group consisting of an aminophenylamidine and the physiologically acceptable acid addition salts thereof, said aminophenylamidine having the formula:

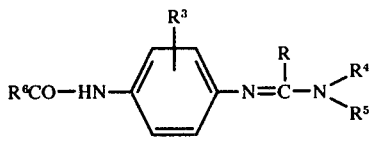

wherein

R is alkyl of 1 to 5 carbon atoms, alkenyl of 2 to 5 carbon atoms or cycloalkyl of 3 to 7 carbon atoms;

$R^3$ is hydrogen, chloro, fluoro, bromo, cyano, trifluoromethyl, alkyl of up to 4 carbon atoms, alkoxy of up to 4 carbon atoms and alkenyl of up to 4 carbon atoms;

$R^4$ is an aliphatic substituent of up to 4 carbon atoms selected from the group consisting of alkyl, alkenyl, alkynyl and alkoxy;

$R^5$ is an aliphatic substituent of up to 4 carbon atoms selected from the group consisting of alkyl or alkenyl, or cycloalkyl of 3 to 7 carbon atoms, and $R^6$ is selected from the group consisting of phenyl, phenoxy, naphthyl, tetralyl, benzyl, phenethyl, benzyloxy, phenylethoxy, phenoxymethyl and phenoxymethoxy, unsubstituted or substituted with 1 to 3 members selected from the group consisting of nitro, trifluoromethyl, hydroxy, cyano, chloro, fluoro, bromo, methyl, methoxy, carbethoxy, methylsulfonyl, acetylamino, or acetyloxy.

2. The compound according to claim 1 which is N-(4-benzoylaminophenyl)-N',N'-dimethylacetamidine.

3. The compound according to claim 1 which is N-(4-(phenoxyacetylaminophenyl)-N',N'-dimethylacetamidine.

4. The compound according to claim 1 which is N-(4-carbobenzoxyaminophenyl)-N',N'-dimethyl-acetamidine.

5. The compound according to claim 1 which is N-(4-carbophenethyloxyaminophenyl)-N',N'-dimethyl-acetamidine.

6. The compound according to claim 1 which is N-(4-phenylacetylaminophenyl)-N',N'-dimethyl-acetamidine.

7. The compound according to claim 1 which is N-(4-phenethylcarbonylaminophenyl)-N',N'-dimethyl-acetamidine.

8. The compound according to claim 1 which is N-(4-benzoylaminophenyl)-N'-methyl-N'-methoxy-acetamidine.

9. The compound according to claim 1 which is N-(4-phenylacetylaminophenyl)-N-methyl-N'-methoxyacetamidine.

10. The compound according to claim 1 which is N-[4-(3-chloro-6-acetyloxybenzoylamino)-phenyl]-N',N'-dimethyl-acetamidine.

* * * * *